(12) United States Patent
Gochin et al.

(10) Patent No.: US 7,438,797 B2
(45) Date of Patent: Oct. 21, 2008

(54) METHOD OF CONTROLLING ASPHALTENE PRECIPITATION IN A FLUID

(75) Inventors: Rodney John Gochin, Tadworth (GB); Alec Smith, Shotwick (GB)

(73) Assignee: iC16 Limited, London (GB)

( * ) Notice: Subject to any disclaimer, the term of this patent is extended or adjusted under 35 U.S.C. 154(b) by 721 days.

(21) Appl. No.: 10/485,390

(22) PCT Filed: Jul. 26, 2002

(86) PCT No.: PCT/GB02/03439
§ 371 (c)(1),
(2), (4) Date: May 5, 2004

(87) PCT Pub. No.: WO03/012253
PCT Pub. Date: Feb. 13, 2003

(65) Prior Publication Data
US 2005/0082231 A1    Apr. 21, 2005

(30) Foreign Application Priority Data
Jul. 31, 2001 (GB) ................. 0118660.0
Jun. 27, 2002 (GB) ................. 0214906.0

(51) Int. Cl.
E21B 37/06 (2006.01)
C10G 75/04 (2006.01)
C09K 8/524 (2006.01)

(52) U.S. Cl. ............... 208/39; 208/44; 208/45; 208/309; 507/90

(58) Field of Classification Search .......... 585/24, 585/26; 208/44, 45, 39, 309
See application file for complete search history.

(56) References Cited

U.S. PATENT DOCUMENTS

| | | | |
|---|---|---|---|
| 3,172,473 A | 3/1965 | Smith et al. | |
| 3,276,519 A | 10/1966 | Knox et al. | |
| 3,485,756 A | 12/1969 | Gee | |
| 4,428,818 A | 1/1984 | Derbyshire et al. | |
| 4,441,890 A | 4/1984 | Feldman | |
| 4,513,155 A * | 4/1985 | Tamura et al. | ......... 585/13 |
| 4,921,619 A | 5/1990 | Karydas | |
| 5,021,498 A | 6/1991 | Stephenson et al. | |
| 5,214,224 A | 5/1993 | Comer et al. | |
| 5,382,728 A * | 1/1995 | Del Bianco et al. | ......... 585/24 |
| 5,690,176 A * | 11/1997 | Delbianco et al. | ......... 166/304 |
| 6,048,904 A * | 4/2000 | Wiehe et al. | ......... 516/20 |
| 6,270,653 B1 * | 8/2001 | Gochin et al. | ......... 208/44 |
| 6,368,422 B1 * | 4/2002 | Breuer et al. | ......... 134/40 |
| 6,599,868 B2 * | 7/2003 | Dunn et al. | ......... 508/482 |

FOREIGN PATENT DOCUMENTS

| | | |
|---|---|---|
| EP | 0 258 179 B1 | 1/1991 |
| GB | 1 523 597 A | 9/1978 |
| WO | WO 95/20637 | 8/1995 |
| WO | WO 98/30784 A | 7/1998 |

OTHER PUBLICATIONS

Database WPI, Section Ch., Week 9647, Derwent Publications Ltd., London, GB; XP002062251 & RU 2 055 088 C (Oil Ind Chem Res Inst), Feb. 27, 1996.
Database WPI, Section Ch, Week 9428, Derwent Publications Ltd., London, GB, XP002062252 & SU 1 813 778 A (Chernogorneft Enterprise), May 7, 1993.
Lobanova et al., "Preventing formation of asphaltene-resin-paraffin deposits", Database WPI, Derwent Publications Ltd., London, GB; AN 1993-225735, XP002220542 & SU 1 749 224 A (Soyuzneftepromkhim Res. Prodn. Assoc.), Jul. 23, 1992, abstract.
Boelhouwer et al., "Viscosity of organic liquids", Applied Scientific Research A, vol. 2, 1950, pp. 249-268, XP001119416.

* cited by examiner

*Primary Examiner*—Ellen M. McAvoy
(74) *Attorney, Agent, or Firm*—Foley & Lardner LLP

(57) ABSTRACT

A method of reducing the aggregation and deposition of asphaltene from a fluid containing asphaltene, such as crude oil, which method comprises the addition to the fluid of a compound of formula (1): wherein A is an optionally substituted ring system containing 6 to 14 carbon atoms; n is at least 1 and may equal the number of positions available for substitution in A; each X is independently a linker group; and each R is independently a hydrocarbyl group containing 10 to 25 carbon atoms.

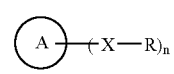

(I)

29 Claims, No Drawings

METHOD OF CONTROLLING ASPHALTENE PRECIPITATION IN A FLUID

The present invention relates to a method of reducing and controlling asphaltene aggregation and deposition from crude oil and the use of certain compounds in such a method.

Asphaltene fractions are defined operationally as that portion of crude oil or bitumen which precipitates on addition of a low molecular weight paraffin (usually n-pentane or n-heptane) but which is soluble in toluene. Asphaltenes are brown to black amorphous solids with complex structures, involving carbon, hydrogen, nitrogen, oxygen and sulphur and are basically formed of condensed aromatic nuclei associated with alicyclic groups. The particles are often surrounded by resins which are considered to add to dispersion stability. The molecular weight of asphaltene ranges from one thousand to several hundred thousand with a particle density of approximately 1200 kg/m$^3$ and a spheroidal shape about 10 nm in diameter.

Asphaltenes are present in oil in quantities up to 15% and are usually stable in their natural environment. However when the oil is moved during the production process, large changes in pressure, temperature and phase composition often occur. This destabilises the asphaltene, leading to aggregation and deposition of the particles as a layer on the surfaces of reservoir rock pores, production piping etc. causing blockages and reduced or no oil flow. Clearing such blockages results in a loss of production and is costly in manpower and materials. Often solvents such as toluene are used but disposal of asphaltene solutions from such cleaning processes can lead to further environmental and health and safety costs. Whilst not prevalent in the North Sea deposits, colloidal asphaltene precipitation from petroleum reservoir fluids is recognised to present serious problems in numerous crude oil systems world-wide leading to significant excess costs in the production operations of the oil industry in for example North America and the Middle East.

Previously compounds have been proposed which purport to be useful in controlling asphaltene aggregation. However these compounds have proved difficult and expensive to manufacture and consequently in spite of their advantages in terms of reduced environmental impact they may not prove successful in replacing the traditional method of dissolving asphaltene blockages in a solvent such as toluene and disposing of the contaminated waste effluent.

Accordingly there remains a need for an efficient, cost effective method of controlling the deposition of asphaltene particles from crude oil onto surfaces such as sandstone rock (and other types of reservoir rock containing silica and silicate minerals) and the steel of wellbore and crude oil handling systems, such as pipelines, valves and storage tanks.

Thus, the present invention provides a method of reducing the aggregation and deposition of asphaltene from a fluid containing asphaltene, such as crude oil, which method comprises the addition to the fluid of a compound of formula (I):

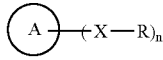

(I)

wherein A is an optionally substituted ring system containing 6 to 14 carbon atoms; n is at least 1 and may equal the number of positions available for substitution in A; each X is independently a linker group; and each R is independently a hydrocarbyl group containing 10 to 25 carbon atoms.

A particular important advantage of the compounds of formula (I) is that they are surprisingly cost effective to source and manufacture compared to previous compounds which have purported activity in the field of controlling asphaltene aggregation. The compounds of the present invention may also have improved properties in terms of reducing aggregation and deposition of asphaltene from fluids such as crude oil.

This invention is applicable to any asphaltene-containing "oil" or "hydrocarbon", wherein these terms are meant to include unrefined and refined hydrocarbonaceous products derived from petroleum or from liquefaction of coal, both of which may contain sulphur compounds; these terms include, particularly for petroleum based fuels, wellhead condensate as well as crude oil which may be contained in storage facilities at the producing field and transported from those facilities by barges, pipelines, tankers, or trucks to refinery storage tanks, or, alternatively, may be transported directly from the producing facilities through pipelines to the refinery storage tanks; these terms also include refined products, interim and final, produced in a refinery, including distillates such as gasolines, kerosenes, diesel fuels, aviation fuels, marine fuels, naphthas, gas oils, distillate fuels, oils, residues, residual fuels, fuel oils, and plant charges. Preferably this invention is applicable to crude oil.

The present invention may also have utility as an additive in reducing particulate and/or soot emission during combustion, particularly the combustion of diesel fuels. Moreover, the compounds of formula (I) may reduce fouling of petroleum apparatus particularly catalyst apparatus.

Whilst the present method is effective in reducing aggregation and deposition of asphaltene from fluids such as crude oil, the method also has efficacy in reducing the precipitation of asphaltene that is or may be dissolved in crude oil in its natural state. The present method is also effective in the presence of waxes and similar particles found in oil which often cause problems in production processes.

The compound of formula (I) is an amphipathic molecule primarily consisting of two active parts; an adsorbing part (ring system A), which sticks to the surface of the asphaltene particle and which carries a long chain (X-R) attached to the ring. A is a primarily aromatic, largely flat molecule whose ring(s) give sufficient interactions through van der Waal's forces to attach itself to the similarly aromatic asphaltene. Thus it provides an anchor for the chain which is much longer and extends into the oil. The chain, being primarily aliphatic, is surrounded by a good solvent, such as oil, and adopts an attitude with many possible conformations while attached to the asphaltene particle at one end through the ring system A.

Thus, without being bound by theory, it is believed that when asphaltene particles coated with compounds of formula (I) collide with each other or with a coated pipe or rock surface, there is interference between the extended chains leading to repulsion. This is because the chain has many possible conformations in the oil leading to high entropy. Interference with a similar chain attached to another asphaltene particle leads to fewer possible conformations and hence a lowering of entropy. Since the change in free energy, $\Delta G$, of a system contains the term minus temperature (T) times change in entropy, $\Delta S$, then a decrease in entropy leads to an increase in free energy, that is repulsion according to the law $\Delta G = \Delta H - T.\Delta S$. Moreover, other things being equal a higher temperature (T) will enhance the term $T.\Delta S$ and lead to a greater chain to chain repulsion. This will be a significant increase in the effect for many oils, which are produced at temperatures between 80° and 200° C.

The chain attached to ring system A should be as long as possible to act at the greatest distance but must retain solubility in the oil. Too long and it will not be sufficiently soluble in the oil and hence will not have free movement lowering the contribution to entropic repulsion. A short chain, while soluble, produces a smaller entropy reduction on interaction. Chain lengths of between 12 and 18 carbon atoms will give the repulsion effect with the optimum at 16 (hexadecyl). While branched chains will also give a repulsive effect, straight chains will produce a greater efficiency. Although the position of the chain on the ring system A is unlikely to have any significant influence on the efficiency of the compounds of formula (I), the presence of two or even more chains attached to differing positions, may increase its effectiveness.

The term "hydrocarbyl group" as used herein denotes a radical having a carbon atom directly attached to the remainder of the molecule. Preferably the hydrocarbyl group contains between 12 and 20 carbon atoms. Hydrocarbyl groups include the following:

(1) Aliphatic hydrocarbon groups; that is, alkyl groups such as decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl; alkenyl groups containing a single double bond such as undecenyl, dodecenyl, tridecenyl, pentadecenyl, hexadecenyl, heptadecenyl, heneicosenyl; alkenyl groups containing 2 or 3 double bonds such as 8,11-hexadecadienyl and 8,11,14-hexadecatrienyl, and alkynyl groups containing a triple bond. All isomers of these are included, but straight chain groups are preferred.

(2) Substituted aliphatic hydrocarbon groups; that is groups containing non-hydrocarbon substituents which, in the context of this invention, do not alter the predominantly hydrocarbon character of the group. Those skilled in the art will be aware of suitable substituents; examples include halogen, nitro, cyano, COOR' (where R' is H or $C_{1-6}$alkyl) or a salt thereof hydroxy and $C_{1-6}$ alkoxy.

(3) Hetero groups; that is, groups which, while having predominantly aliphatic hydrocarbon character within the context of this invention, contain atoms other than carbon present in a chain or ring otherwise composed of aliphatic carbon atoms. Suitable hetero atoms will be apparent to those skilled in the art and include, for example, oxygen, nitrogen and sulphur.

Preferably the hydrocarbyl group, R, is a $C_{12-20}$ alkyl chain, more preferably a $C_{14-18}$ alkyl chain, With $C_{16}$ being especially preferred. In a most preferred embodiment R is n-hexadecyl (n-$C_{16}H_{33}$). It will be appreciated that R may be a straight or branched chain. Preferably R is a straight chain.

The term "linker group" as used herein denotes any organic moiety that may serve to attach the hydrocarbyl group, R, to the ring system A. For example, the linker group may be a methylene group (—$CH_2$—), a carbonyl group (—CO—), an oxygen atom, a nitrogen atom, a sulphur atom, an ester group (—$CO_2$—), an alkyl ether group, an alkyl thio group, an alkyl amino group, an alkyl carboxy group or an alkyl ester group. In certain embodiments the linker group may form part of the ring system, for example if the ring system were an indole then the linker group may be the indole nitrogen atom. Preferably the linker group is an ether link, a thio ether link, an amine link, an alkyl ether group, an alkyl thio group or an alkyl amino group. More preferably the linker group is an ether link, a thio ether link or an amine link with an ether link being most preferred. When A is naphthalene, the linker group is preferably attached at the 1 or 2 position, most preferably the 2 position.

The term "alkyl" as used in the definition of "linker group" denotes a saturated straight or branched alkyl chain containing from 1 to 6 carbon atoms. Examples of such groups include without limitation methyl, ethyl, n-propyl, isopropyl, n-butyl, iso-butyl, sec-butyl, tert-butyl, neopentyl and hexyl. Preferably the term "alkyl" as used in the definition of "linker group" denotes a straight or branched alkyl chain containing from 1 to 4 carbon atoms, with n-methylene, n-ethylene, n-propylene and n-butylene being most preferred.

The term "ring system" as used herein denotes a system comprising from 1 to 3 rings, at least one of which should be aromatic. When there is more than one ring, the rings may be fused or linked by a single bond, preferably the rings are fused. Optionally the ring system may contain one or more heteroatoms selected from nitrogen, oxygen or sulphur, with nitrogen being most preferred. In one embodiment the ring system contains one to three heteroatoms, most preferably one nitrogen atom. In a preferred embodiment A is an aromatic carbocyclic ring system selected from benzene, naphthalene and anthracene. Naphthalene is especially preferred; it is more strongly adsorbed on asphaltenes than benzene and has fewer environmental and safety problem associated with it than either benzene or anthracene.

A may be optionally substituted in positions not occupied by X. Such substitutions should not interfere with the properties of the compound. Suitable substituents may include $C_{1-6}$ alkyl groups such as methyl, ethyl, propyl, iso-propyl, n-butyl, iso-butyl, sec-butyl or t-butyl; or $C_{1-6}$ haloalkane such as fluoromethyl, difluoromethyl, trifluoromethyl, chloromethyl, dichloromethyl, trichloromethyl, 2-fluoroethyl, 2,2,2-trifluoromethyl and pentafluoroethyl. Preferably the total number of substituents on ring system A is no more than about 5 or 6; once the number of substituents is greater than about 5 or 6, the adsorption of the ring system A on the asphaltene particle's surface may become impaired.

Preferably n is 1, 2 or 3. More preferably n is 1. When n is 2 or more, the X and R groups may be the same or different. Preferably n is 2 and both R groups are n-hexadecyl.

In a preferred embodiment A is naphthalene, X is selected from a $C_{1-4}$ alkyl ether group, an $C_{1-4}$ alkyl thio group and an $C_{1-4}$ alkyl amino group, n is 1 and R is a $C_{12-16}$ alkyl chain. In another preferred embodiment A is naphthalene, X is selected from an ether link, an amine link or an thio ether link, n is 1 and R is a $C_{14-18}$ alkyl chain. In another preferred embodiment A is naphthalene, X is selected from an ether link, an amine link or an thio ether link, n is 1 and R is a $C_{16}$ alkyl chain. In a most preferred embodiment A is naphthalene, X is an ether link, n is 1 and R is n-hexadecyl. Further preferred embodiment are set out in the table below:

| Example | A | n | X | R |
| --- | --- | --- | --- | --- |
| 1 | Naphthalene | 1 | Ether | n-hexadecyl |
| 2 | Benzene | 2 | Ether/Ether | n-hexadecyl/$C_{14-18}$ alkyl |
| 3 | Naphthalene | 2 | Ether/Amine | n-hexadecyl/n-hexadecyl |
| 4 | Naphthalene | 1 | Ether | $C_{12-20}$ alkyl |
| 5 | Benzene | 1 | Amine | $C_{14-18}$ alkyl |
| 6 | Naphthalene | 1 | Thiol | $C_{14-18}$ alkyl |
| 7 | Anthracene | 1 | Ether | n-hexadecyl |
| 8 | Naphthalene | 1 | methyl ether | $C_{14-18}$ alkyl |
| 9 | Naphthalene | 1 | methyl thio | $C_{14-18}$ alkyl |
| 10 | Naphthalene | 1 | methyl amine | $C_{14-18}$ alkyl |

-continued

| Example | A | n | X | R |
|---|---|---|---|---|
| 11 | Naphthalene | 1 | ethyl ether | $C_{12-16}$ alkyl |
| 12 | Naphthalene | 1 | ethyl thio | $C_{12-16}$ alkyl |
| 13 | Naphthalene | 1 | ethyl amine | $C_{12-16}$ alkyl |
| 14 | Naphthalene | 1 | propyl ether | $C_{12-16}$ alkyl |
| 15 | Naphthalene | 1 | propyl thio | $C_{12-16}$ alkyl |
| 16 | Naphthalene | 1 | propyl amine | $C_{12-16}$ alkyl |
| 17 | Naphthalene | 1 | butyl ether | $C_{12-14}$ alkyl |
| 18 | Naphthalene | 1 | butyl thio | $C_{12-14}$ alkyl |
| 19 | Naphthalene | 1 | butyl amine | $C_{12-14}$ alkyl |
| 20 | Naphthalene | 2 | $C_{1-4}$ alkyl ether/ $C_{1-4}$ alkyl ether | $C_{14-18}$ alkyl/ $C_{14-18}$ alkyl |
| 21 | Naphthalene | 2 | $C_{1-4}$ alkyl thio/ $C_{1-4}$ alkyl thio | $C_{14-18}$ alkyl/ $C_{14-18}$ alkyl |
| 22 | Naphthalene | 2 | $C_{1-4}$ alkyl amine/ $C_{1-4}$ alkyl amine | $C_{14-18}$ alkyl/ $C_{14-18}$ alkyl |
| 23 | Naphthalene | 2 | $C_{1-4}$ alkyl ether/ $C_{1-4}$ alkyl amine | $C_{14-18}$ alkyl/ $C_{14-18}$ alkyl |
| 24 | Naphthalene | 1 | carbonyl group | $C_{14-18}$ alkyl |
| 25 | Naphthalene | 1 | ester group | $C_{14-18}$ alkyl |

Although whilst it is possible for the compounds of formula (I) to be used directly in the method of the present invention, preferably the compounds of formula (I) are first dissolved in a carrier fluid. Accordingly, in a further aspect, the present invention provides a solution comprising a compound of formula (I) and a carrier fluid. Suitably the compound of formula (I) and the carrier fluid are present in a ratio of about 1:100. In a preferred method of reducing aggregation and deposition of asphaltene from crude oil the solution comprising the compound of formula (I) in a carrier fluid is pumped down the oil shaft into the well during the drilling process using conventional technology. An effective amount of a compound of formula (I) for use in the present invention may be readily ascertained by the skilled person. Suitably an effective amount of a compound of formula (I) for use with present invention will range from 10 to 10,000 g per ton of crude oil.

As mentioned above, previous compounds which purport to be useful in controlling asphaltene aggregation have the disadvantage that they can be difficult and/or expensive to manufacture in that the requisite starting materials and reagents may be hazardous, difficult to obtain and expensive either in themselves or when the cost of safe disposal of waste materials is calculated. For example, 2-hexadecyl naphtalene which has been proposed as a asphaltene aggregation inhibitor may be prepared by Friedel-Craft's acylation of naphthalene with 2-hexadecanoyl chloride (palmitoyl chloride) in the presence of anhydrous aluminium chloride and nitrobenzene using the method of Buu-Hoi & Cagnint (Bull. Soc. Chim., 12 (1945) p307) followed by Wolff-Kishner reduction of the resultant 2-hexadecanoyl naphthalene using the Huaing-Min-lon modification (Anderson JACS)(1953) p449). However, this conversion requires the use of expensive and hazardous reagents and gives rise to a waste stream which is costly to dispose of safely. An alternative and potentially cheaper route is to use a commercial catalyst such as Envirocat EPZ10 (Contract Chemicals, Knowsley, UK) which should allow the direct attachment of an alkyl halide molecule to naphthalene. However such alkylation reactions often result in a mixture of isomeric products which prove difficult and costly to separate.

In contrast at least some of the compounds of the present invention are relatively easy and cost effective to prepare safely. The compounds of formula (I) may be prepared by methods well known to those skilled in the art. For example, compounds of formula (I) may be prepared by reacting a compound of formula (II):

wherein A is as defined previously and X' is a linker group precursor moiety, for example when X is an ether link X' is hydroxy, when X is an secondary amine link X' is a primary amine group, when X is a thio ether link X' is a thiol and when X is an alkyl ether link X' is alkyl hydroxy etc, with a compound of formula (III):

wherein R is as defined previously and L is a leaving group such as a halogen atom or an alkyl or aryl sulphonate under appropriate conditions. The reaction may be carried out by directly mixing the reagents, preferably the reaction is carried out in a solvent. Advantageously the reaction may be carried out at elevated temperature and/or in the presence of a base.

Thus, when X is an ether link the compounds of formula (I) may be produced fairly easily by reacting naphthol with an alkyl chloride. Naphthol is a cheap readily available bulk chemical and this type of 'Williamson' synthesis is inexpensive. Similarly when X is nitrogen or sulphur the starting materials are naphthylamine or naphthalene thiol and an alkyl halide.

It will be appreciated by those skilled in the art that the compounds of the present invention are intended to be manufactured on an industrial scale, in a cost effective manner. Accordingly it may prove an economic necessity that starting materials used in the manufacturing process are not isolated pure compounds but are in fact a mixture of more than one compound. Such starting mixtures will produce a combination of products. For example, in the reaction exemplified below the naphthol may be a mixture of 1-naphthol and 2-naphthol whilst the hexadecyl halide may include other $C_{12-20}$, preferably $C_{14-18}$ alkyl halides. Product mixtures of such reactions are intended to be within the scope of the present invention. Preferably product mixes for use in the methods of the present invention comprises more 50% of a single compound of formula (I), more preferably 75%, most preferably more than 90%.

EXAMPLE 1

Preparation of Hexadecyl Naphthoxide

To a dry round bottom flask charged with naphthol (10.21 g) in THF (100 mL) at 0° C. was added sodium hydride (2.72 g, 60% dispersion in oil) portion wise. After complete addition of the sodium hydride, hexadecyl chloride (18.48 g) was added carefully over 30 mins, the ice bath removed and the temperature allowed to rise to room temperature. After stirring at room temperature for 2 hours the reaction mixture was poured onto ether (200 mL)/sodium hydroxide (100 mL 0.5N). The aqueous layer was separated and extracted with ether (50 mL×2). The combined organic layers were washed with water (50 mL ×2) dried [$MgSO_4$] and concentrated in vacuo to yield the crude title compound.

EXAMPLE 2

Determination of Asphaltene Dispersion in Crude Oils

It is generally accepted that asphaltenes exist in petroleum oil as particles in a dispersed state, colloidally stabilised at least to some extent by the resins which act as peptizing agents. Resin molecules surround asphaltene particles and can form a layer giving a steric shield. If this protective shield is removed by for instance the dissolution of the resins into the fluid phase, the asphaltene particles start to aggregate into larger particles (i.e. coagulate) which can result in asphaltene deposition onto surfaces. The presence of compounds of formula (I) will reduce the instability of asphaltenes by mimicking the action of resins for maximum effectiveness in aliphatic solvents such as crude oil. The stabilisation of asphaltene particles occurs when the compounds of formula (I) are attached to the surfaces of asphaltene particles by the carbocyclic heads and stretch the hydrocarbyl chains out into the oil to form a steric stabilisation layer. Though this will only happen to maximum effect in an aliphatic liquid which is good solvent for the hydrocarbyl chain such as oil, it should however be partially effective in solvents such as toluene.

The particle size distribution of a solid in crude oil can not be easily determined by conventional techniques. A laser back-scattering technique was developed to avoid the difficulty in strongly absorbing dispersion media such as crude oil. The technique uses photon correlation spectroscopy, also called quasi elastic light scattering, but in the back-scatter mode rather than the more conventional forward scattering. This is particularly useful for concentrated dispersions or for strongly absorbing solutions as in this work. The instrument used in this work was supplied by Brookhaven Instruments, New York. The particle detection range was from 2 nm up to 10 μm. The instrument was supplied with a fibre optic probe to allow measurements in remote locations. Despite the relative sophistication of such an instrument, the measurement of particle size distribution remains difficult if the fluid has strongly absorbing characteristics like crude oil. This is because a considerable amount of laser light is absorbed and the intensity of back-scattered light can be very weak. In our version of the Brookhaven instrument, in order to go through a thick window in high pressure cells the optical probe was modified to give a focus point distance from the probe tip to the centre of the scattering volume of about 4 mm. Two different cells were designed to carry out measurements of asphaltene particle sizes in oil. The first cell was designed in rectangular shape from black (carbon filled) PTFE with a 3.8 mm thick push fit quartz window. The other cell consists of a cylindrical housing made from thick plastic material with a window (quartz) held in one end of the cylindrical housing. With this technique the size distributions of asphaltene particles may be monitored in the presence of a compound of formula (I).

The invention claimed is:

1. A method of reducing the aggregation and deposition of asphaltene from a fluid containing asphaltene, such as crude oil, which method comprises the addition to the fluid of a compound of formula (I):

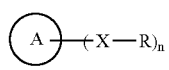

(I)

wherein A is naplhthalene; n is at least 1 and may equal the number of positions available for substitution in A; each X is independently a $C_{1-4}$ alkyl ether group, a $C_{1-4}$ alkyl thio group, a $C_{1-4}$ alkyl amino group, an ether link, an amine link, a thio ether link, a carbonyl (—CO—) link or an ester (—$CO_2$—) link; and each R is independently a hydrocarbyl group containing 10 to 25 carbon atoms.

2. A method according to claim 1 wherein X is selected from an ether, an amine or a thio ether link, n is 1 and R is a $C_{14-18}$ alkyl chain.

3. A method according to claim 1 wherein X is selected from a $C_{1-4}$ alkyl ether group, a $C_{1-4}$ alkyl thio group or a $C_{1-4}$ alkyl amino group, n is 1 and R is a $C_{12-16}$ alkyl chain.

4. A method according to claim 1 wherein X is selected from a carbonyl group or an ester group, n is 1 and R is a $C_{14-18}$ alkyl chain.

5. A method according to claim 1 wherein X is an ether link, n is 1 and R is n-hexadecyl.

6. A method according to claim 1 wherein n is 2, both X's are ether and both R's are different $C_{14-18}$ alkyl chains.

7. A method according to claim 1 wherein n is 2, both X's are ether, and both R's are n-hexadecyl.

8. A method according to claim 1 wherein the compound of formula (I) is a mixture of compounds of formula (I).

9. A method according to claim 1 wherein n is at least 1 and may equal the number of positions available for substitution in A; each X is independently an ether link, an amine link, a thio ether link, a carbonyl (—CO—) link or an ester (—$CO_2$—) link.

10. A method according to claim 1, wherein the fluid containing asphaltene is crude oil.

11. A solution comprising a compound of formula (I):

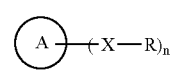

(I)

wherein A is naphthalene; n is at least 1 and may equal the number of positions available for substitution in A; each X is independently a $C_{1-4}$ alkyl ether group, a $C_{1-4}$ alkyl thio group, a $C_{1-4}$ alkyl amino group, an ether link, an amine link, a thio ether link, a carbonyl (—CO—) link or an ester (—$CO_2$—) link; and each R is independently a hydrocarbyl group containing 10 to 25 carbon atoms and a carrier fluid.

12. A solution according to claim 11 wherein the compound of formula (I) is a mixture of the compounds of formula (I) and a carrier fluid.

13. A solution according to claim 11 wherein n is at least 1 and may equal the number of positions available for substitution in A; each X is independently an ether link, an amine link, a thio ether hnk, a carbonyl (—CO—) link or an ester (—$CO_2$—) link.

14. A solution according to claim 11 wherein X is selected from either, an amine or a thio ether link, n is 1 and R is a $C_{14-18}$ alkyl chain.

15. A solution according to claim 11 wherein X is selected from a $C_{1-4}$ alkyl ether group, a $C_{1-4}$ alkyl thio group or a $C_{1-4}$ alkyl amino group, n is 1 and R is a $C_{12-16}$ alkyl chain.

16. A solution according to claim 11 wherein X is selected from a carbonyl group or an ester group, n is 1 and R is a $C_{14-18}$ alkyl chain.

17. A solution according to claim 11 wherein X is an ether link, n is 1 and R is n-hexadecyl.

18. A solution according to claim 11 wherein n is 2, both X's are ether and both R's are different $C_{14-18}$ alkyl chain.

19. A solution according to claim 11 wherein n is 2, both X's are ether and both R's are n-hexadecyl.

20. A method of preventing asphaltene precipitation in a fluid containing asphaltene which method comprises addition to the fluid of a compound of formula (I):

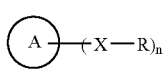
(I)

wherein A is naphthalene; n is at least 1 and may equal the number of positions available for substitution in A; each X is independently a $C_{1-4\ alkyl}$ ether group, a $C_{1-4}$ alkyl thio group, a $C_{1-4}$ alkyl amino group, an ether link, an amine link, a thio ether link, a carbonyl (—CO—) link or an ester (—$CO_2$—) link; and each R is independently a hydrocarbyl group containing 10 to 25 carbon.

21. A method according to claim 20 wherein n is at least 1 and may equal the number of positions available for substitution in A; each X is independently an ether link, an amine link, a thio ether link, a carbonyl (—CO—) link or an ester (—$CO_2$—) link.

22. A method according to claim 20 wherein X is selected from an ether, an amine or a thio ether link, n is 1 and R is a $C_{14-18}$ alkyl chain.

23. A method according to claim 20 wherein X is selected from a $C_{1-4}$ alkyl ether group, a $C_{1-4}$ alkyl thio group or a $C_{1-4}$ alkyl amino group, n is 1 and R is a $C_{12-16}$ alkyl chain.

24. A method according to claim 20 wherein X is selected from a carbonyl group or an ester group, n is 1 and R is a $C_{14-18}$ alkyl chain.

25. A method according to claim 20 wherein X is an ether link, n is 1 and R is n-hexadecyl.

26. A method according to claim 20 wherein n is 2, both X's are ether and both R's are different $C_{14-18}$ alkyl chain.

27. A method according to claim 20 wherein n is 2, both X's are ether and both R's are n-hexadecyl.

28. A method according to claim 20 wherein the compound of formula (I) is a mixture of compounds of formula (I).

29. A method according to claim 20, wherein the fluid containing asphaltene is crude oil.

* * * * *